United States Patent [19]

Young

[11] Patent Number: 5,199,871
[45] Date of Patent: Apr. 6, 1993

[54] ACTUATOR FOR A CONTROL VALVE OF A DENTAL SYRINGE

[75] Inventor: Barry S. Young, Tualatin, Oreg.

[73] Assignee: DCI International, Inc., Newberg, Oreg.

[21] Appl. No.: 862,740

[22] Filed: Apr. 3, 1992

[51] Int. Cl.⁵ ............................................. A61G 17/02
[52] U.S. Cl. ..................................................... 433/80
[58] Field of Search ...................... 433/80, 84, 85, 87, 433/100; 251/322, 900

[56] References Cited

U.S. PATENT DOCUMENTS

| | | | |
|---|---|---|---|
| 3,401,691 | 9/1968 | Beu | 433/80 |
| 3,640,304 | 2/1972 | Fox et al. | 433/80 X |
| 3,652,053 | 3/1972 | Poitras et al. | 251/322 X |
| 3,874,083 | 4/1975 | Buckley | 433/80 |
| 4,026,025 | 5/1977 | Hunt | 433/80 |
| 4,227,878 | 10/1980 | Lohn | 433/80 |
| 5,045,055 | 9/1991 | Gonser et al. | 251/322 X |

*Primary Examiner*—Gene Mancene
*Assistant Examiner*—Nicholas D. Lucchese
*Attorney, Agent, or Firm*—Trask, Britt & Rossa

[57] ABSTRACT

An actuator for a control valve of a dental syringe having a body including a button having a head larger than the diameter of a passageway in which the actuator is to be installed to actuate a control valve of the syringe, a shoulder closely fitting in the passageway, a shaft smaller than the shoulder and having an O-ring snugly fitted therearound and the O-ring also fitting into a groove provided therefor in the passageway, a valve stem engaging portion and a tapered collar extending from the shaft to the valve stem engaging portion to provide for easy O-ring installation.

6 Claims, 2 Drawing Sheets

ACTUATOR FOR A CONTROL VALVE OF A DENTAL SYRINGE

BACKGROUND OF THE INVENTION

2. Field

This invention relates to control valves for dental syringes and the like. It is particularly related to valves suitable for the control of air or water through a dental syringe and operable, through a valve actuator, with the same hand with which the syringe is held by a user during dental operations.

2. State of the Art

As is shown in U.S. Pat. No. 4,026,025, it is known to position pushbutton-type actuators on the top of the head of a dental syringe. So positioned, the actuators can be conveniently manipulated to operate control valves internal the syringe. These valves in turn regulate the flow of air and water through the syringe head, and eventually to and through a syringe tip.

The '025 patent discloses a syringe head and tip unit that is typical of other known structures. In general, such units include a syringe head with air and/or water conduit connector(s). Air and/or water are each supplied under pressure through individual connectors to respective passageways in the head. A flow control valve is mounted in each such passageway. A separate passageway and flow control valve is provided for each connector. Thus, if a single air or water connector is provided, a single passageway and a single flow control valve will be present. Alternatively, if both air and water connectors are provided, separate valves will be present within each of two respective passageways.

The control valve provided for each passageway used is generally biased to its closed condition. It has been found that the valve unit commonly used in pneumatic tire stems (i.e., a Schrader valve), is a very suitable control valve for dental syringes. A typical dental syringe structure includes a Schrader valve threaded into the passageway between a connector and its associated outlet to the syringe tip.

A valve actuator is also mounted within and projects from the passageway. It is thus positioned for operation by a user selectively and intermittently to open the control valve. An open valve allows the flow of a utility from the connector to the tip.

U.S. Pat. No. 4,026,025 discloses a valve actuator which comprises a monolithic button with an O-ring fitted in a slot encircling the button. The button is inserted into the passageway, and friction between the O-ring and the passageway wall is relied upon to hold the button in place. One end of the button projects from the passageway, and is curved to accommodate finger feel of the user, while the opposite end is provided with a depression configured to receive an end of the actuator stem of the control valve. In use, the button and O-ring reciprocate together in the passageway, and the O-ring seals the unit to prevent flow past the button.

The valve actuator of the '025 patent is generally depressed by pressure applied to the top curved end by a user's thumb. When the pressure is released, the control valve is closed by a valve spring. The valve spring must also function to push the button further out of the passageway as the valve closes. Because only the frictional engagement between the O-ring and the passageway wall holds the button in the passageway, it is possible for the button to escape from its installed position. It may be inadvertently dislodged and pulled from the syringe head or it may fall from the head. Such an occurrence is especially likely after the button has been repeatedly removed and reinserted into the head. Under those circumstances, the O-ring tends to become worn.

SUMMARY OF THE INVENTION

The present invention provides a valve actuator for use in a dental syringe having either a single or a plurality of utility passageways and associated control valves. The present valve actuator, when inserted into a passageway of a dental syringe head, is mechanically locked in the passageway. The locking mechanism currently of choice is an O-ring fitted into a groove provided in the wall of the passageway. An actuator of more or less conventional construction is installed such that its shaft is positioned to reciprocate through the O-ring. The valve is actuated by depressing a button portion at one end of the shaft of the actuator. A spring is positioned between the housing of the control valve and a collar formed on the shaft of the actuator. Upon release of actuating pressure, the button is expelled by action of the spring to its stopped location corresponding to the normally closed condition of the valve.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENT

Figure 1:
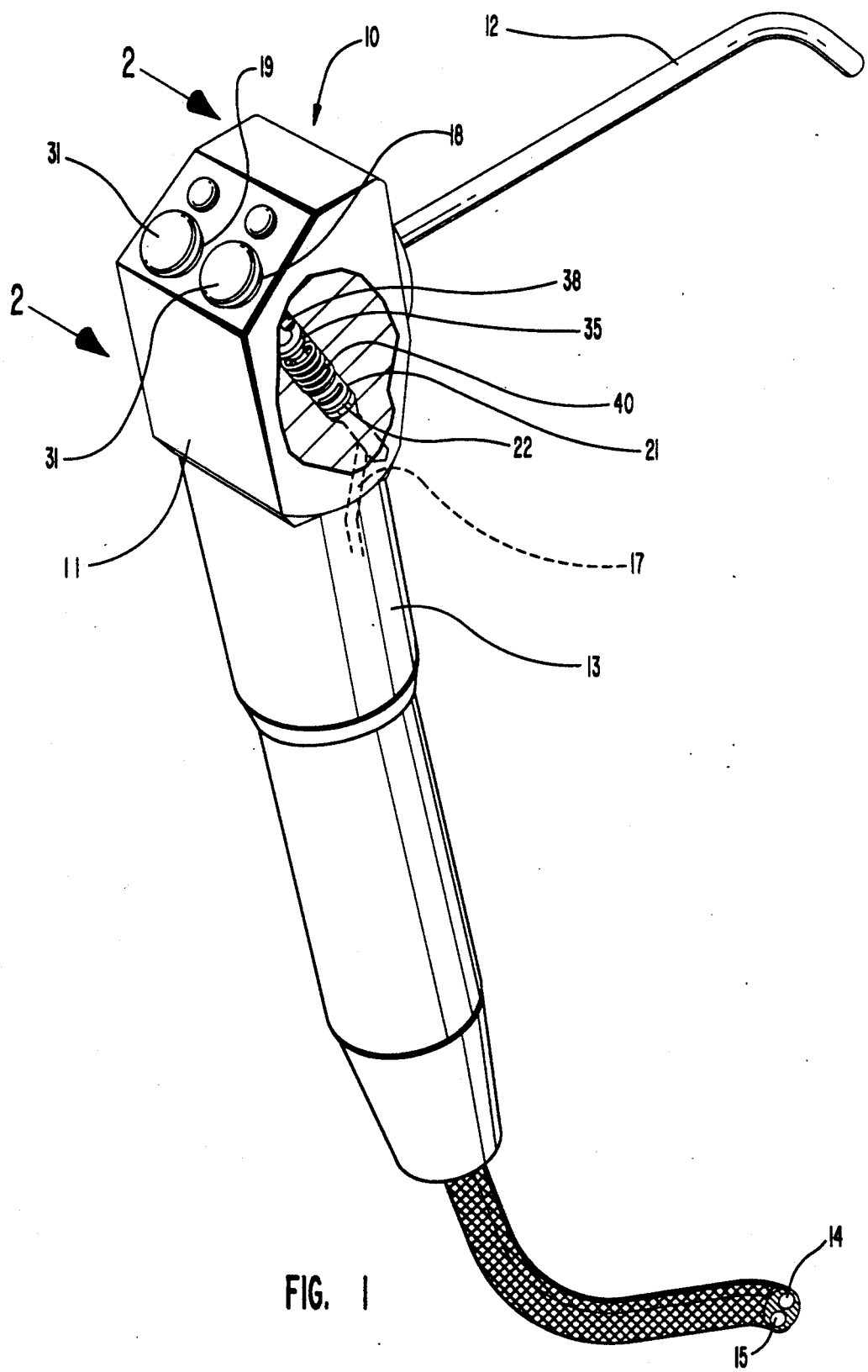
FIG. 1 is a perspective view, partially broken away, of a dental syringe incorporating the valve actuator of the invention.

Referring to FIG. 1, a dental syringe, designated generally 10, includes a syringe head 11, with a removable syringe tip 12 and a projecting handle 13.

An air conduit 14 and a water conduit 15 provide air and water, respectively, to channels 16 and 17, that open into inlet ends of passageways 18 and 19, respectively, formed in the syringe head. Ports 20A and 20B interconnect the respective passageways 18 and 19 with respective bores 21A and 21B through the syringe tip 12.

Each of the passageways 18 and 19 is interiorly threaded at 22 to receive an exteriorly threaded control valve 23. The control valve is preferably of the type conventionally used with pneumatic tires, is normally biased closed and has a projecting valve stem 23A that is pushed inwardly with respect to the valve to open the valve and to allow flow between a connector 16 or 17 and the appropriate port 20A or 20B connected to the syringe tip 12. The valve stem 23A thus constitutes means for operating the valve 23 intermittently to its open condition.

Each passageway 18 and 19 communicates with an integral groove 24 in the sidewall 25 which defines the passageway 18, 19. A valve actuator 30 is inserted into each passageway to provide means for actuating the control valve 23 in the passageway. The valve actuator 30 is preferably constructed in one-piece, and includes a pushbutton 31, having a rounded top surface 31a and a diameter larger than that of the passageway. A shoulder 32, which projects from the button 31, has a diameter just smaller than that of the passageway 18, 19 so that the shoulder will fit snugly into and will reciprocate within the passageway. A shaft 33, of reduced diameter, projects from the shoulder 32, and terminates in a collar 34. The collar 34 includes a portion 35 with a diameter greater than that of shaft 33 and then is tapered, to a smaller diameter, as the collar extends away from the shaft 33, to a valve stem contact member 36.

An O-ring 38 fits snugly, both in the groove 24 and around the shaft 33. The shaft 33 reciprocates through the O-ring 38, but movement of the valve actuator 30 is limited by engagement of the shoulder 32 and collar 34 with the O-ring 38.

The O-ring 38 is installed on the valve actuator 30 by stretching it over the collar 34. The tapered configuration of the collar greatly facilitates installation of the O-ring, with the O-ring stretching as it is rolled over the collar and onto the stem. Thereafter, the valve actuator 30 is installed in the passageway by inserting it, valve stem contact member 36 first, until the O-ring expands into the groove 24.

Figure 2:
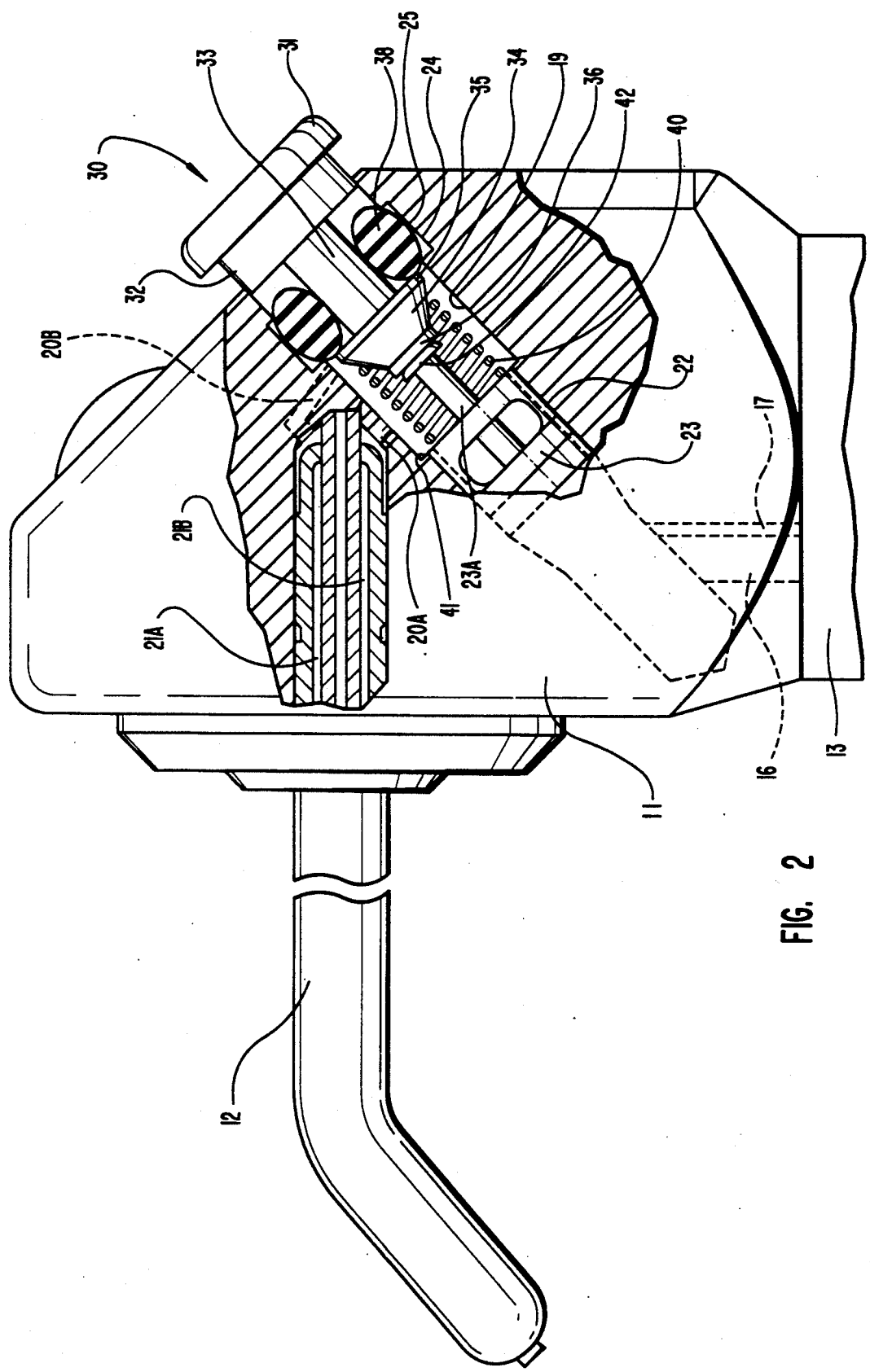
FIG. 2 is a fragmentary side elevation view of the head portion of the dental syringe of FIG. 1, partially broken away to show the valve actuator in its installed condition within the head.

A coil spring 40 may be provided between the surface 41 of the housing of control valve 23 and the collar 34. The spring 40 is positioned around the valve stem 23A before the valve actuator 30 is inserted into the passageway 19 (FIG. 2).

During use of the syringe 10, the control valve 23 is normally closed and there is no fluid flow through the syringe head to the syringe tip. An operator grasping handle 13 uses a thumb or finger to push on button 31, thereby to force the shoulder 32, shaft 33, collar 34 and valve stem contact member 36 further into the passageway 19. This movement causes valve stem contact member 36 to engage a projecting end 42 of valve stem 23A. The resulting axial movement of the valve stem 23A opens the valve 23 and allows flow through the syringe head and out the syringe tip 12. When the operator releases the button 31, the pressure of fluid flow through the valve 23 and the biasing action of spring 40 moves the valve actuator 30 away from the valve stem 23A, and the valve 23 is biased closed to again prevent flow through the syringe head.

The O-ring 38 is sufficiently elastic that it will compress as the valve actuator 30 is installed in the passageway 19, and will then expand to extend into the groove 24. The O-ring 38 cooperates with the groove 24 to hold the valve actuator 30 against inadvertent withdrawal from the syringe head. Nevertheless, the valve actuator 30 can be removed from the passageway 19 by grasping the button 31 and pulling with sufficient force to pull the O-ring 38 from groove 24.

Reference herein to the details of the illustrated embodiment is by way of example only and is not intended to limit the scope of the appended claims, which themselves recite those details regarded as important to the invention.

I claim:

1. In a dental syringe having a syringe head with a passageway therein and a normally closed valve in said passageway, said valve having a valve stem projecting therefrom for operating said valve, a valve actuator system comprising: a wall member defining said passageway; a groove in said wall member encircling said passageway;
   a body, including a button having a diameter larger than the diameter of said passageway, a shoulder projecting from said button and having a diameter just less than the diameter of said passageway, a shaft having first and second ends, projecting at said first end from said shoulder towards said valve and having a diameter smaller than that of said shoulder, and a collar at said second end of said shaft, a portion of said collar having a diameter larger than the diameter of the shaft; and
   an O-ring sealingly fitted around said shaft for reciprocation of said shaft therethrough and sized to extend beyond the diameter of said shoulder, whereby said O-ring extends sealingly and is fixedly held within said groove and is held in said groove against undesired movement with said shaft when said body is inserted into said passageway.

2. The valve actuator system of claim 1, wherein said collar is tapered inwardly away from said shaft.

3. The valve actuator system of claim 2, further including:
   a valve stem contact member on the end of said collar remote from said shaft, said valve stem contact member being separate from said valve stem and aligned therewith to engage said valve stem upon pushing of said button towards said valve stem.

4. A dental syringe comprising:
   a syringe head having a passageway therein, said passageway having inlet and outlet ends, means for supplying fluid to said inlet end, a normally closed valve in said passageway, said valve having a valve stem constituting means for operating said valve intermittently to its open condition, a discharge port extending from said passageway at said outlet end, and a groove encircling said passageway and formed in a wall of said passageway;
   a syringe tip coupled to said syringe head and having a bore therethrough connected to said discharge port;
   a valve actuator including a button having a diameter large than the diameter of said passageway, a shoulder having a diameter just less than the diameter of said passageway and projecting from said button, a shaft having a diameter smaller than that of said shoulder and projecting from said shoulder towards said valve stem, and a collar at the distal end of said shaft, said collar having a portion thereof of a diameter larger than the diameter of said shaft; and
   an O-ring sealingly fitted around said shaft between said shoulder and said collar for reciprocation of said shaft therethrough and sized to extend beyond said shoulder and which is fixedly held within said groove in said passageway to be held in said groove against undesired movement with said shaft.

5. A syringe as in claim 4, further including a coil spring encircling said valve stem and positioned between said valve and said collar to thereby bias said collar away from said valve stem.

6. In a dental syringe having a syringe head with a passageway therein and a normally closed valve in said passageway, said valve having a valve stem projecting therefrom for operating said valve, a valve actuator system comprising: a groove integral with and encircling said passageway;
   a body, including a button having a diameter larger than the diameter of said passageway, a shoulder projecting from said button and having a diameter just less than the diameter of said passageway, and a shaft having first and second ends, projecting at said first end from said shoulder and having a diameter smaller than that of said shoulder and a collar at the second end of said shaft to engage said valve stem; and an O-ring sealingly fitted around said shaft between said shoulder and said collar and sized to extend beyond the outer diameter of said shoulder, whereby said O-ring extends into and is fitted and held within said groove and is held in said groove against undesired movement with said shaft when said body is inserted into said passageway with said button remaining external said passageway.

* * * * *